US007320879B2

(12) United States Patent
Karlsson et al.

(10) Patent No.: US 7,320,879 B2
(45) Date of Patent: Jan. 22, 2008

(54) METHOD OF DETERMINING SITE-SPECIFICITY AND KIT THEREFOR

(75) Inventors: Robert Karlsson, Uppsala (SE); Helena Nordin, Uppsala (SE); Susanna Nyberg, Ramlösa (SE)

(73) Assignee: Biacore AB, Uppsala (SE)

( * ) Notice: Subject to any disclaimer, the term of this patent is extended or adjusted under 35 U.S.C. 154(b) by 391 days.

(21) Appl. No.: 10/722,061

(22) Filed: Nov. 25, 2003

(65) Prior Publication Data

US 2004/0166549 A1 Aug. 26, 2004

Related U.S. Application Data

(60) Provisional application No. 60/430,244, filed on Dec. 2, 2002.

(30) Foreign Application Priority Data

Dec. 2, 2002 (SE) .................................. 0203548

(51) Int. Cl.
*G01N 1/30* (2006.01)
(52) U.S. Cl. .................................................. 435/40.5
(58) Field of Classification Search ............... 435/40.5, 435/4, 7.91; 436/518
See application file for complete search history.

(56) References Cited

U.S. PATENT DOCUMENTS

| 5,372,783 | A | * | 12/1994 | Lackie | 422/68.1 |
|---|---|---|---|---|---|
| 5,824,500 | A | * | 10/1998 | Bandman et al. | 435/69.1 |
| 6,100,098 | A | * | 8/2000 | Newkirk | 436/507 |
| 6,121,055 | A | * | 9/2000 | Hargreaves | 436/526 |
| 6,849,397 | B2 | * | 2/2005 | Nelson et al. | 435/5 |
| 7,112,326 | B2 | * | 9/2006 | Yan et al. | 424/146.1 |

FOREIGN PATENT DOCUMENTS

| WO | WO 94/28416 | 12/1994 |
|---|---|---|
| WO | WO 97/18472 | 5/1997 |
| WO | WO 2004/040309 A1 | 5/2004 |

OTHER PUBLICATIONS

Magali et al., "Determination of the Association and Dissociation Rate Constants of Muscarinic Antagonists on Rat Pancreas: Rank Order of Potency Varies with Time", Molecular Pharmacology, 36: 405-411, 1989.*

Motulsky et al., "The Kinetics of Competitive Radioligand Binding Predicted by the Law of Mass Action", Molecular Pharmacology, 1984.*
Flatmark et al., "Tyrosine hydroxylase binds tetrahydrobiopterin cofactor with negative cooperativity, as shown by kinetic analyses and surface plasmon resonance detection", Eur. J. Biochem. 262, 840-849 (1999).*
Frostell-Karlsson, A. et al., "Biosensor Analysis of the Interaction Between Immobilized Human Serum Albumin and Drug Compound for Prediction of Human Serum Albumin Binding Levels," *J Med Chem.* 43(10):1986-92, May 2000.
Martin, C. et al., "Communication Between Multiple Drug Binding Sites on P-Glycoprotein," *Molecular Pharmacology* 58(3):624-632, 2000.
Nordin, H. et al., "Characterization of Low Molecular Weight Compound Binding to Kinases Using Non-Label SPR Biosensors," *Biacore Poster presented at the Screentech® World Summit*, San Diego, CA, Mar. 2003.
Nordin, H. et al., "Kinase Studies Using Biacore," *Application note BR-9003-58*, Sep. 2003.
Rich, R. et al., "High-Resolution and High-Throughput Protocols for Measuring Drug/Human Serum Albumin Interactions Using BIACORE," *Analytical Biochemistry* 296:197-207, 2001.
McNally et al., "A Library of Monoclonal Antibodies to *Escherichia coli* K-12 Pyruvate Dehydrogenase Complex," J. Biol. Chem. 270(34):19744-19751, 1995.

* cited by examiner

*Primary Examiner*—Ann Y. Lam
(74) *Attorney, Agent, or Firm*—Yonggang Ji

(57) ABSTRACT

The invention relates to a method of determining the binding site specificity of an analyte to a ligand having at least two different binding sites, which method comprises immobilizing the ligand to a solid support, mixing the analyte with a reversibly binding reference analyte which has a dissociation behaviour that differs significantly from that of the analyte, contacting the mixture with the ligand to determine dissociation characteristics for the mixture, and determining therefrom the binding site specificity of the analyte in relation to the reference analyte. The invention also relates to an analytical system for carrying out the method, and to a computer program, computer program product and computer system for performing the method.

16 Claims, 10 Drawing Sheets

METHOD OF DETERMINING SITE-SPECIFICITY AND KIT THEREFOR

CROSS-REFERENCES TO RELATED APPLICATIONS

This application claims the benefit of U.S. Provisional Application No. 60/430,244 filed Dec. 2, 2002, and also claims priority to Swedish Application No. 0203548-3 filed Dec. 2, 2002, both of which applications are incorporated herein by reference in their entirety.

BACKGROUND OF THE INVENTION

1. Field of the Invention

The present invention relates to a method of determining the site-specificity for the binding of an analyte to a ligand having more than one binding site, as well as to a kit for carrying out the method. The invention also relates to an analytical system, a computer program product and a computer system for performing the method.

2. Description of the Prior Art

An important function of blood proteins is to permit reversible binding of ligands, such as fatty acids, hormones, amino acids, cations, etc, to ensure that they are distributed throughout the body. Therefore, when a drug is administered to a living body it is usually bound to a smaller or larger extent to blood (plasma) proteins. The unbound drug concentration in plasma is therefore being more closely related to the pharmaceutical activity than the total concentration of drug. The major protein in plasma responsible for binding of many kinds of drugs is human serum albumin (HSA). There are at least six different binding sites spread over the HSA molecule and to which drug molecules may bind. Determining the binding propensity of a drug candidate to HSA is therefore essential in evaluating drug candidates. Traditionally, binding properties have been examined using techniques such as equilibrium dialysis, fluorescence, circular dichroism, column chromatography, or titration calometry. Recently, also surface plasmon resonance (SPR) biosensors have been used (Frostell-Karlsson, Å, et al., *J. Med. Chem.* 43, 1986-1992; Rich, R., et al., *Anal. Biochem.*, 296, 197-207).

In addition to the binding parameters, it is also important to know to which specific binding site on the HSA molecule that the drug candidate binds. For example, co-administration of drugs which share the same binding site can cause an increase in the unbound drug concentrations due to binding competition, and may result in undesirable side effects or unexpected changes in drug disposition. To identify the binding site, X-ray crystallography may be used. Alternatively, site-specificity may be determined by studying competition with substances whose site specificities are already known, using techniques, such as, for example, circular dichroism, microcalometry or affinity blotting. While no such determination of a drug candidate's HSA-binding site by competitive SPR biosensor techniques seems to have been reported in the literature, the use of SPR biosensor technology may, of course, also be contemplated.

Naturally, there are numerous other ligands than HSA that have more than one binding site and for which it may be of interest to determine the site-specificity of drug candidates and other binding species.

U.S. Pat. No. 5,753,518 discloses the use of mass-sensing methods, especially SPR biosensor technology, to determine the binding of low molecular weight analytes, such as drugs, to a common receptor (ligand) immobilized to a sensing surface. The molecular weights of the analytes are often considered to be too low to give detectable responses when binding to the sensing surface. Each low molecular weight analyte is therefore mixed with an analyte analogue having a substantially higher molecular weight than the low molecular weight analyte, the mixture is contacted with the surface, and the response of each mixture is compared with that of the analyte analogue alone. The distorsion of the analyte analogue response (lowering of the response level) is representative of the affinity and kinetic properties of the low molecular weight analyte. While the response usually is in the form of a binding curve (response vs. time), it is not necessary to study the response up to steady state or equilibrium but the initial part of the association phase is sufficient.

It is an object of the present invention to provide an improved method of determining the binding site specificities of analytes to a ligand having multiple binding sites.

BRIEF SUMMARY OF THE INVENTION

The above and other objects and advantages are provided by a method and kit, respectively, for determining the binding site specificity of a reversibly binding analyte to a ligand (such as a biomolecule) having multiple binding sites, which method and kit are based upon mixing the analyte with a reference analyte that binds reversibly to a binding site of the ligand (usually the binding site is known, meaning that a defined binder is known to bind thereto), contacting the mixture with the ligand, and (as opposed to studying association response levels as in the prior art surface competitive methods) studying the dissociation phase after the contact of the mixture with the ligand has stopped. More particularly, the present invention is based upon selecting the reference analyte such that the dissociation phase behaviour thereof differs significantly from that of the analyte by being either substantially faster or substantially slower, and determining if the dissociation phase of the component having the slower dissociation phase behaviour may be reduced or eliminated by an increased concentration of the component having the faster dissociation phase behaviour (thereby inhibiting binding to the ligand of the component having the slower dissociation phase behaviour if they both would have the same binding site specificity).

In one aspect, the present invention therefore relates to a method of determining the binding site specificity of an analyte that binds to a ligand having at least two different binding sites, which method comprises the steps of:

immobilizing the ligand to a solid support, providing a reference analyte which binds reversibly to the ligand at a (usually known) binding site thereof and whose dissociation phase after interaction with the ligand is either substantially faster or substantially slower than that of the analyte, contacting a mixture of the analyte and the reference analyte with the immobilized ligand to permit association to the ligand, the concentration of the one of the analyte and the reference analyte that has the faster dissociation phase being sufficient to at least substantially inhibit binding to the ligand of the one having the slower dissociation phase, should the analyte and the reference analyte both bind to the same binding site on the ligand, stopping the contacting of the analyte and the reference analyte with the ligand to permit dissociation therefrom, determining a dissociation-related value for the mixture at at least one pre-selected time during the dissociation phase, and determining from the determined dissociation-related value or values for the mixture if the contribution to this value or values from the one of the analyte and the reference analyte that has the slower dissociation phase is suppressed, substantial suppression indicating that the analyte and the reference analyte bind to the same binding site, and substantial absence of suppression indicating that the analyte and the reference analyte bind to different binding sites.

The procedure is preferably repeated with at least one additional mixture of the analyte with another reference analyte that binds specifically to a different binding site on the ligand.

The term "ligand" as used herein means an entity that has a known or unknown affinity for a given analyte. The ligand may be a naturally occurring species or one that has been synthesized. The ligand is usually a biomolecule, e.g., a drug target, such as a membrane receptor.

The term "analyte" as used herein refers to a molecule whose binding to the ligand is to be determined. For the purposes of the present invention, the analyte is often a low molecular weight compound.

The term "immobilizing" as used herein means binding by covalent or non-covalent binding through one or more attachment sites. The term also includes, e.g., immobilizing a ligand to a solid support by capturing the ligand by an agent immobilized to the solid support.

The term "dissociation phase" as used herein refers to both the period of time after dissociation has started until dissociation essentially has stopped or at least decreased to a considerable degree, and to the behaviour of a species or mixture of species bound to the biomolecule and dissociating during this time period.

The term "dissociation-related value" as used herein means a measurement value that is representative of the momentary residual binding on the ligand after dissociation has started. Usually, it is the momentary binding level. A series of binding levels measured at different times will form a binding curve.

In another aspect, the present invention relates to a kit for carrying out the method, which kit comprises at least one reference analyte capable of binding specifically in a reversible defined manner to a defined binding site of a ligand with multiple binding sites.

In still another aspect, the present invention provides an analytical system for studying molecular interactions, which comprises data processing means for performing the above method.

In yet another aspect, the present invention provides a computer program comprising program code means for performing the method.

In still another aspect, the present invention provides a computer program product comprising program code means stored on a computer readable medium or carried on an electrical or optical signal for performing the method.

In yet another aspect, the present invention provides a computer system containing a computer program comprising program code means for performing the method.

These and other aspects of the invention will be evident upon reference to the accompanying drawings and the following detailed description.

DETAILED DESCRIPTION OF THE INVENTION

As mentioned above, the present invention generally relates to the determination of the site-specificity of an analyte that binds reversibly to a ligand, such as a biomolecule, having at least two different analyte binding sites. Surface binding interactions may be characterized using a number of different analysis interaction techniques. Recently, label-free biosensor technology has become a powerful tool for such interaction analysis. Commercially available biosensors include the BIACORE®) system instruments, marketed by Biacore AB, Uppsala, Sweden, which are based on surface plasmon resonance (SPR) and permit monitoring of surface interactions in real time.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
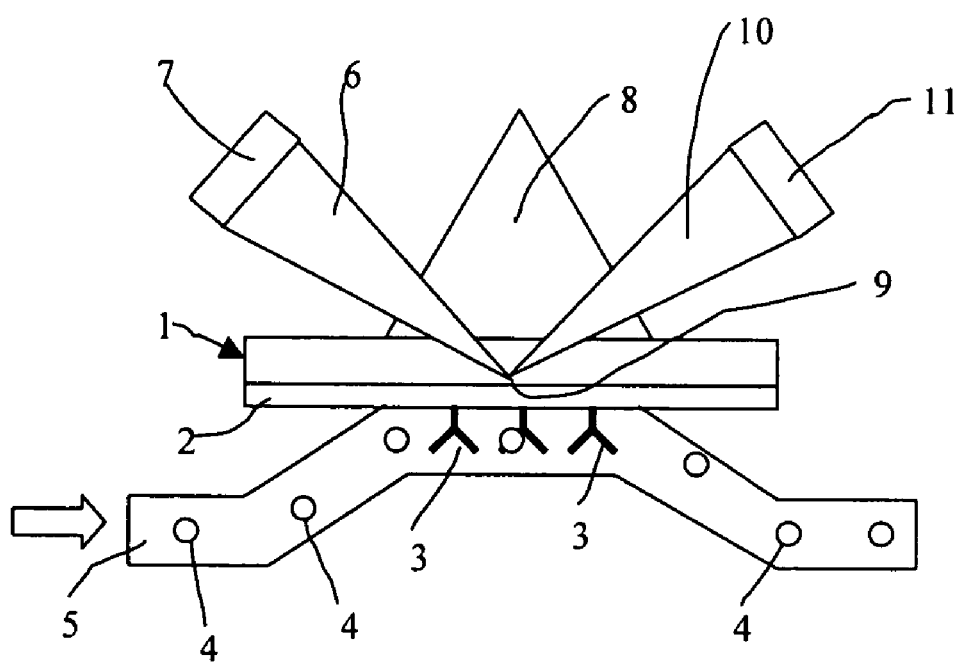
FIG. 1 is a schematic side view of a biosensor system based on SPR.

A schematic illustration of the BIACORE® system is shown in FIG. 1. Sensor chip 1 has a gold film 2 supporting capturing molecules 3, e.g., antibodies, exposed to a sample flow with analytes 4 (e.g., an antigen) through a flow channel 5. Monochromatic p-polarised light 6 from a light source 7 is coupled by a prism 8 to the glass/metal interface 9 where the light is totally reflected. The intensity of the reflected light beam 10 is detected by an optical detection unit 11.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the BIACORE® system, the SPR response values are expressed in resonance units (RU). One RU represents a change of 0.0001° in the angle of minimum reflected light intensity, which for most proteins is roughly equivalent to a change in concentration of about 1 pg/mm² on the sensor surface. As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicated on the sensorgram by a drop in RU over time as analyte dissociates from the surface-bound ligand.

Figure 2:
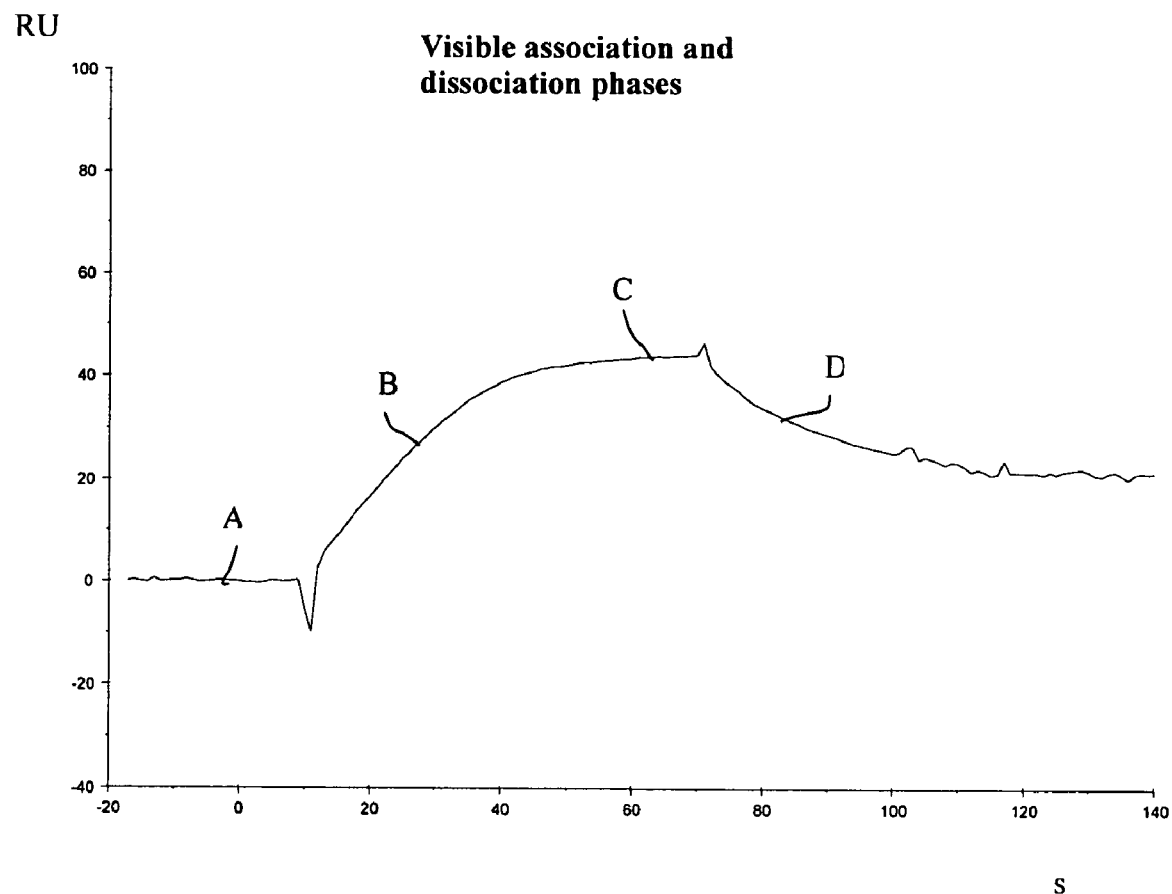
FIG. 2 is a representative sensorgram where the binding curve has visible association and dissociation phases.

A representative sensorgram (binding curve) for a reversible interaction at the sensor chip surface is presented in FIG. 2, the sensing surface having an immobilized capturing molecule, for example an antibody, interacting with analyte in a sample. The vertical axis indicates the response (here in resonance units, RU) and the horizontal axis indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached where the resonance signal plateaus at C. At the end of sample injection, the sample is replaced with a continuous flow of buffer and a decrease in signal reflects the dissociation, or release, of analyte from the surface. This part D of the binding curve is usually referred to as the "dissociation phase". The slope of the association/dissociation curve provides valuable information regarding the interaction kinetics, and the height of the resonance signal represents surface concentration (i.e., the response resulting from an interaction is related to the change in mass concentration on the surface).

Assume a reversible reaction (which is not mass transfer limited) between an analyte A and a surface-bound (immobilized) capturing molecule B (first order kinetics):

$$A+B \Leftrightarrow AB$$

The rate of change in surface concentration of A during analyte injection is $$\frac{d\Gamma}{dt} = k_{ass}(\Gamma_{max} - \Gamma)C - k_{diss}\Gamma$$

where $\Gamma$ is the concentration of bound analyte, $\Gamma_{max}$ is the maximum binding capacity of the surface, $k_{ass}$ is the association rate constant, $k_{diss}$ is the dissociation rate constant, and C is the bulk analyte concentration. Rearrangement of the equation gives:

$$\frac{d\Gamma}{dt} = k_{ass}C\Gamma_{max} - (k_{ass}C + k_{diss})\Gamma$$

If all concentrations are measured in the same units, the equation may be rewritten as:

$$\frac{dR}{dt} = k_{ass}CR_{max} - (k_{ass}C + k_{diss})R$$

where R is the response in RU. In integrated form, the equation is:

$$R = \frac{k_{ass}CR_{max}}{k_{ass}C + k_{diss}}(1 - e^{-(k_{ass}C+k_{diss})t})$$

The rate of dissociation can be expressed as:

$$\frac{dR}{dt} = -k_{diss}R$$

and in integrated form:

$$R = R_0 \cdot e^{-k_{diss}t}$$

where $R_0$ is the response at the beginning of the dissociation phase.

Figure 3:
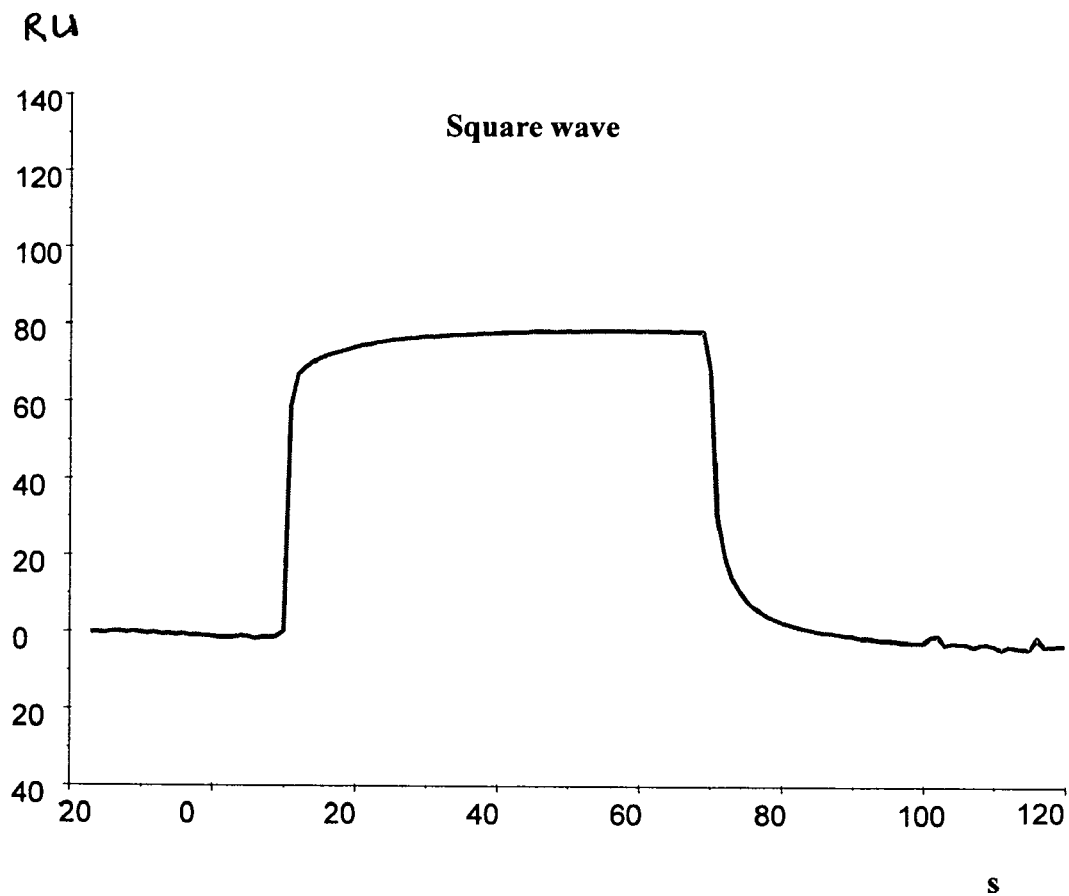
FIG. 3 is a representative sensorgram where the binding curve has the shape of a square wave.

The faster the association and dissociation phases are to and from steady state, or equilibrium, the more will the sensorgram curve have the shape of a square wave or pulse, without visible association and dissociation phases, e.g., as shown in FIG. 3.

Now, assume that two compounds, or analytes, both bind to a ligand, such as a biomolecule, having two different binding sites, and that the association/dissociation behaviour of the two analytes with the biomolecule differ such that one of the analytes has a binding curve with visible association and dissociation phases, corresponding two that shown in FIG. 2, while the binding curve of the other analyte is a square pulse or wave, corresponding to that shown in FIG. 3.

Consider first the alternative of the two analytes competing for the same binding site on the biomolecule. If the concentration of the analyte having the square wave-shaped binding curve (fast dissociation phase) is increased such that it more or less will inhibit binding to the biomolecule of the analyte having the binding curve with visible association and dissociation phases (slow dissociation phase), it has been found that the contribution of the inhibited analyte to the combined dissociation phase characteristic will then be substantially eliminated. The dissociation phase will therefore essentially correspond to that of the square wave-shaped binding curve.

If, on the other hand, the two analytes bind to different binding sites, then both analytes will contribute to the combined dissociation phase. However, as is readily seen, the contribution of the analyte having the square wave-shaped binding curve to the combined dissociation phase will be insignificant, and the resulting dissociation phase will therefore essentially correspond to that of the analyte having the binding curve with visible association and dissociation phases.

Consequently, if the binding site specificity for one of the two analytes is known, that analyte may then be used as a reference analyte to determine if the other analyte binds to the same binding site on the biomolecule or not. The reference analyte may then be the analyte having the square wave-shaped binding curve, or more generally, a faster dissociation phase, and the analyte of unknown binding specificity may be the one having a binding curve with visible association and dissociation phases, or more generally, a slower dissociation phase, or vice versa.

It is readily seen that such use of the shape of the dissociation phase part of the binding curve shape to determine binding site specificity is generally applicable, as long as the dissociation phases of the two analytes differ sufficiently. It is, however, not necessary that one of the analytes has a square wave-shaped binding curve, but the influence of the analyte having the slower dissociation phase on the combined dissociation phase (by inhibited binding of that analyte to the biomolecule) may be determined even if the binding curves of both analytes have visible or discernible association and dissociation phases. The necessary difference in dissociation phases depends on several factors, including the association rate constant ($k_{ass}$), the dissociation rate constant ($k_{diss}$) and the molecular weight ($M_w$) and may readily be determined by the skilled person in each particular case.

Further, and importantly, it is readily seen that it will not be necessary to study the whole, or even a substantial part of the dissociation phase for the analyte mixture and the separate analytes, respectively. Rather, it may be quite sufficient to determine the dissociation level at one or more pre-selected times during the dissociation phase.

In accordance with the above, an analyte having a known site specificity to a certain multivalent ligand and a relatively faster dissociation phase, preferably exhibiting a square wave-shaped binding curve, may be used to determine the site specificity of one or more analytes having a relatively slower dissociation phase, represented by a binding curve(s) with visible association and dissociation phases.

Alternatively, an analyte of known binding site specificity to a certain multivalent ligand and relatively slower dissociation phase, represented by a binding curve with visible association and dissociation phases, may be used to determine the site specificity of one or more analytes having a relatively faster dissociation phase, preferably exhibiting a square wave-shaped binding curve.

It is also possible to use a combination of the above embodiments. For instance, an analyte of known binding site specificity and a faster dissociation phase may first be used to determine the binding specificity of an analyte having a slower dissociation phase. The latter analyte may then in turn be used as a reference analyte to determine the binding site specificity of one or more other analytes having a faster dissociation phase(s).

In a convenient way of carrying out the method of the invention, the concentration of the one of the analyte and the reference analyte having the slower dissociation phase is kept constant while the concentration of the one having the faster dissociation phase is successively increased, and the degree of dissociation (binding level) at a predetermined time (or times) after the dissociation phase has started is measured to determine the possible influence on the combined dissociation phase of increasing the concentration. Alternatively, rather than measuring at a single time, respective binding curves may be produced.

While, basically, the ligand having multiple binding sites may be any such ligand for which it is desired to determine the binding site specificity of one or more analytes, an illustrative example is serum albumin, especially the above-mentioned human serum albumin (HSA). HSA is the most abundant protein in plasma and is responsible for protein binding of many kinds of drugs. Determining a drug candidate's binding propensity for HSA is therefore an important part of preclinical studies of absorption, distribution, metabolism and excretion (ADME).

HSA has several high affinity and low affinity binding sites. There are two major binding sites, usually referred to as the warfarin site (site I) and the benzodiazepine site (site II). Many substances bind to HSA giving a square wave type binding curve in association/dissociation studies. Among those are a number of commercially available pharmaceutical compounds, such as, for example, warfarin, naproxen and digitoxin. Through crystallography studies, warfarin is known to bind to the above-mentioned site I, while naproxen binds to site II. Digitoxin binds to the so-called digitoxin site. These substances may therefore be used to determine the binding site specificity of substances, such as, e.g., drug candidates, which exhibit binding curves with visible association and dissociation phases in association/dissociation studies.

Another illustrative example is protein kinases, which are critical components of signaling pathways, triggering many biological events. They constitute a large family of structurally related enzymes that catalyze the phosphorylation of proteins, i.e., the transfer of a phosphate group from adenosine triphosphate (ATP) or guanosine triphosphate (GTP) to the hydroxyl group of serine, threonine or tyrosine in a substrate protein. To this end the protein kinases have at least one ATP (or GTP) binding site (catalytic site), and at least one substrate binding site (regulatory site). Deregulated protein kinase activity has been implicated in a number of important human diseases, including cancer, diabetes, and disorders of the immune system. Protein kinases have therefore been attractive targets for new therapeutic agents that may be directed to either the catalytic site(s) or the regulatory site(s) of the protein. Determining which binding site of the protein kinase that a drug candidate binds to is therefore of importance.

In case the ligand is a drug target, such as, e.g., the above-mentioned protein kinases, the site specificity determination may be used for drug optimisation.

The above-described method may advantageously be performed using a computer system running software that implements the steps of the method. For example, the software may be in the form of one or more so-called wizards, e.g., a first wizard for immobilizing the ligand, a second wizard for carrying out the assay, and a third wizard for evaluating the resulting assay data. The invention also extends to computer programs, particularly computer programs on or in a carrier, adapted for putting the site specificity determination method of the invention into practice. The carrier may be any entity or device capable of carrying the program. For example, the carrier may comprise a storage medium, such as a ROM, a CD ROM or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded.

A kit for carrying out the method of the invention comprises at least one, but preferably two or more reference analytes, each of which binds specifically to a different binding site of a multi-site target ligand, reversibly and with a defined association/dissociation behaviour (sufficiently different from that (those) of the analyte(s) as mentioned above). Preferably, for each analyte/reference analyte combination, the analyte has a binding curve with visible association and dissociation phases, and the reference analyte has a binding curve with a square wave shape, or vice versa.

Advantageously, there is provided in the kit, for at least one of the binding sites on the ligand, at least one reference analyte whose interaction with the biomolecule can be represented by a binding curve having visible association and dissociation phases, and at least one reference analyte whose interaction with the biomolecule can be represented by a binding curve having a square wave type shape.

In a preferred embodiment, the kit comprises a plurality of pairs of reference analytes, each binding to a different binding site on the ligand and comprising (i) a reference analyte whose interaction with the biomolecule can be represented by a binding curve having visible association and dissociation phases, and (ii) a reference analyte whose interaction with the biomolecule can be represented by a binding curve having a square wave type shape. Preferably, there is provided in the kit one such pair of reference analytes with different properties for each binding site of interest on the ligand.

In another preferred embodiment, the kit additionally comprises a computer program product as described above which contains program code means, e.g., stored on a computer readable medium, for performing the method.

The detection technique used for determining dissociation data in accordance with the present invention may readily be selected by the skilled person from a large number of detection techniques that are presently known, or will be known in the future. A convenient way of performing the method of the present invention is using a biosensor. A biosensor is broadly defined as a device that uses a component for molecular recognition (for example a layer with immobilised antibodies) in conjunction with a solid state physicochemical transducer. Biosensors may be based on a variety of detection methods. Typically such methods include, but are not limited to, mass detection methods, such as piezoelectric, optical, thermo-optical and surface acoustic wave (SAW) device methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, angle, wavelength, polarization, or phase resolved, for example evanescent wave ellipsometry and evanescent wave spectroscopy (EWS, or Internal Reflection Spectroscopy), both may include evanescent field enhancement via surface plasmon resonance (SPR), Brewster angle refractometry, critical angle refractometry, frustrated total reflection (FTR), scattered total internal reflection (STIR)— which may include scatter enhancing labels, optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Biosensor systems based on SPR as well as FTR are commercially available today. Exemplary such SPR-biosensors include the above-mentioned BIACORE® instruments sold by Biacore AB (Uppsala, Sweden). A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE instrument may be found in U.S. Pat. No. 5,492,840. The full disclosures of the above-mentioned U.S. patents are incorporated by reference herein.

In the following Examples, various aspects of the present invention are disclosed more specifically for purposes of illustration and not limitation.

EXAMPLES

Instrumentation

A BIACORE® S51 instrument (Biacore AB, Uppsala, Sweden) was used. This instrument has two Y-type flow cells which allow a dual flow of fluids over a sensor chip surface, so-called hydrodynamic addressing, as described in, for example, EP-B1-1021703 (the disclosure of which is incorporated by reference herein). The instrument uses three parallel detection spots on the sensor chip. As sensor chip was used Series S Sensor Chip CM5 (Biacore AB, Uppsala, Sweden) which has a gold-coated surface with a covalently linked carboxymethyl-modified dextran polymer hydrogel. The output from the instrument is a "sensorgram" which is a plot of detector response (measured in "resonance units", RU) as a function of time. An increase of 1000 RU corresponds to an increase of mass on the sensor surface of approximately 1 $ng/mm^2$.

A. Example 1

Determination of HSA-Binding Site Specificity

Immobilization of HSA on Sensor Chip

HSA (Sigma A-4327, Lot#30K7615; Sigma, U.S.A.) was diluted to 20 µg/ml in 10 mM sodium acetate pH 5.0 and immobilized on sensor chip Series S CM5 according to the manufacturer's instructions using amine coupling with a contact time of 7 minutes and a flow of 10 µl /min. Running buffer was 10 mM phosphate buffer and the temperature was maintained at 25° C.

Site-Specificity Experiments

Sample Preparation

Compounds binding to HSA at a known site with a square wave-like binding curve were mixed with compounds binding to HSA at an unknown site and having a binding curve with visible association and dissociation phases. The compound giving visible association and dissociation phases was kept at a constant concentration and was mixed with a "square wave" compound at different concentrations.

Two compounds having visible association and dissociation phases and unknown HSA-binding sites were used, here referred to as compound S1(Mw 345) and compound S2(Mw 364). The following compounds with visible association and dissociation phases and known HSA-binding sites were used: Warfarin (Mw 308; site I)), naproxen (Mw 230; site II), digitoxin (Mw 765; digitoxin site), phenyloin (Mw 252; site II), sulfadimethoxine (Mw 310; site I), and phenylbutazone (Mw 308; site I), all from Sigma (U.S.A.).

All compounds were provided in stock solutions of 10 mM in 100% DMSO, and were diluted with DMSO and PBS. Each "square wave" compound was then mixed with the "association-dissociation" compounds S1 and S2 to produce respective concentration series where S1 was kept at a constant concentration of 0.1 µM, and S2 at a concentration of 0.25 µM. The concentration of the "square-wave" compound in each series was varied from 0-200 µM for warfarin, naproxen and digitoxin, and from 0-50 µM for phenyloin, sulfadimethoxine and phenylbutazone. The final concentration of DMSO was 5% in all samples to match the assay buffer.

Assays

Running buffer was 10 mM phosphate buffer, 5% DMSO, pH 7.4, and the temperature was 25° C. Each run started with a conditioning cycle with three injections of 50 mM NaOH followed by three start-up cycles with buffer. Calibration cycles were run every other concentration series with 8 correction points (4.5-5.8% DMSO). The samples in the concentration series were run in the order of increasing concentration. Each cycle consisted of a 60 s injection of the sample, a 30 s dissociation phase, a stabilization period of 30 s, a buffer injection of 60 s to check for carry-over and a wash with 50% DMSO, all at flow 30 µl/min. A positive control, 30 µM warfarin (Sigma A-2250), and a negative control, 5% DMSO, were injected between every concentration series.

Figure 4:
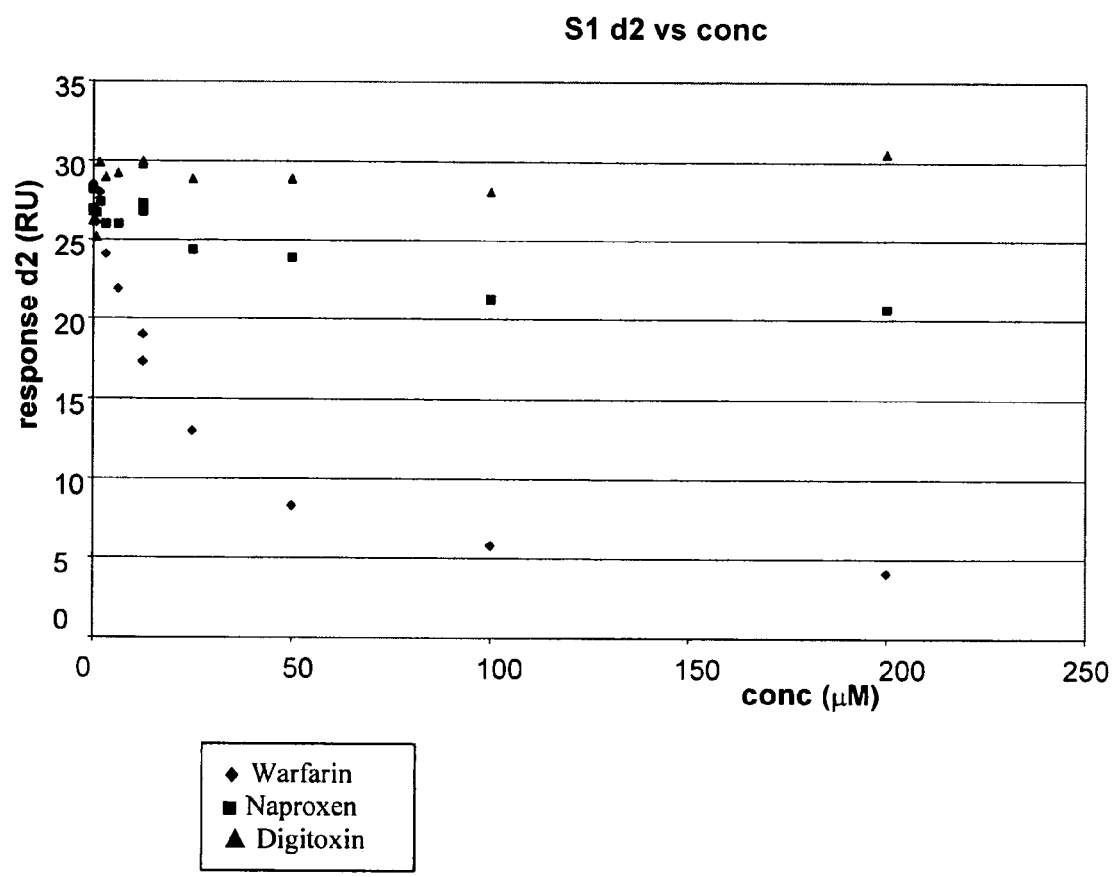
FIG. 4 is a plot of response at a defined dissociation time vs. concentration for the binding to HSA of mixtures of an analyte (S1) with three different reference ligands (warfarin, naproxen and digitoxin, respectively).
Figure 5:
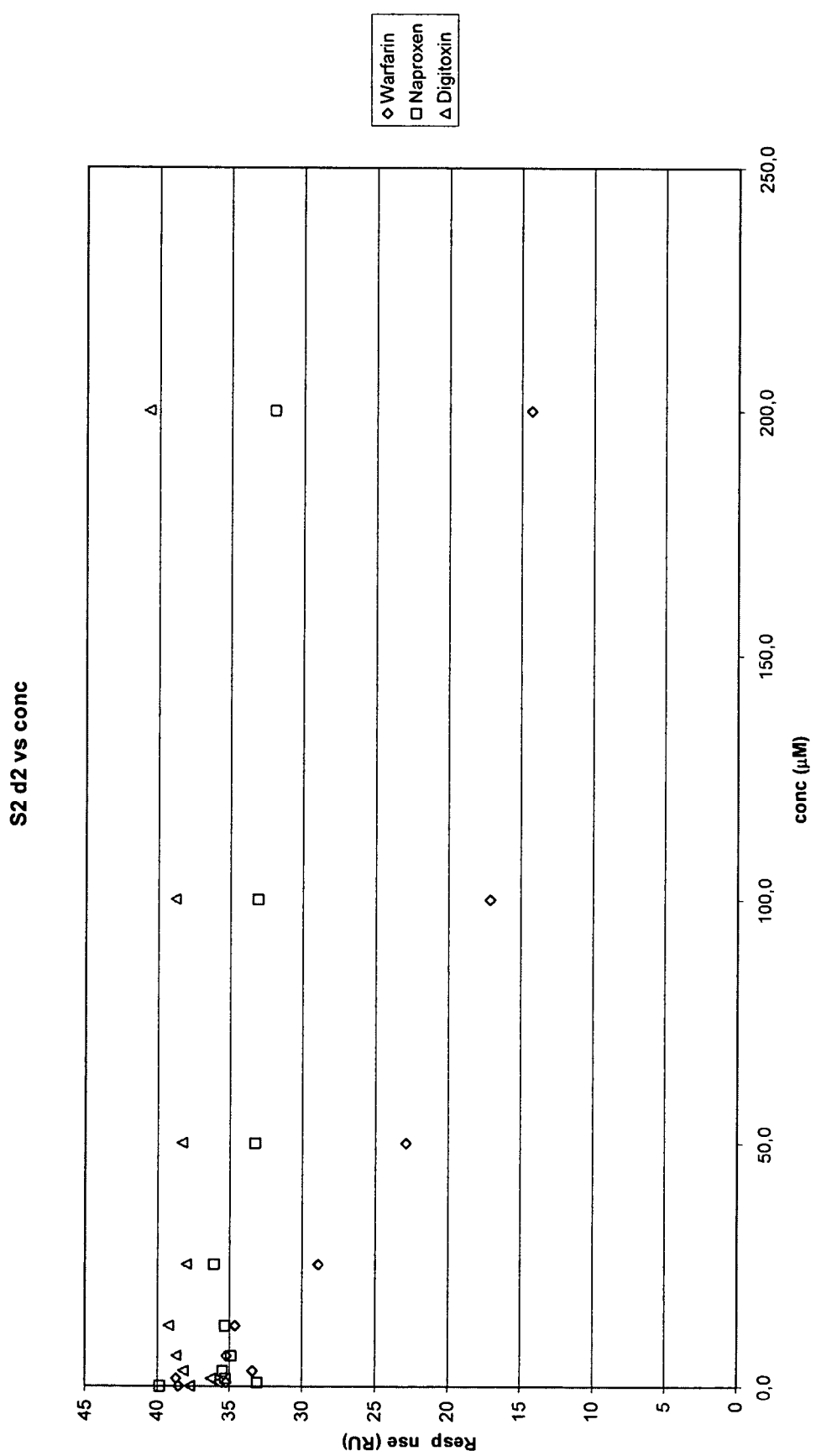
FIG. 5 is a plot of response at a defined dissociation time vs. concentration for the binding to HSA of mixtures of an analyte (S2) with three different reference ligands (warfarin, naproxen and digitoxin, respectively).

The above protocol was first run with mixtures of compounds S1 and S2, respectively, with warfarin, naproxen and digitoxin. The response in the stability late report point (d2-point) was plotted against concentration of compounds S1 and S2, respectively, and the results are shown in FIG. 4 for S1, and in FIG. 5 for S2. As appears from FIG. 4, warfarin is inhibiting the binding of S1 rather effectively, while naproxen inhibits it to some degree. Digitoxin, on the other hand, does not seem to affect the dissociation phase much. This implies that S1 and warfarin mainly bind to the same site. FIG. 5 demonstrates that compound S2 also is inhibited by warfarin, indicating that S2 binds to the same site as warfarin.

Figure 6:
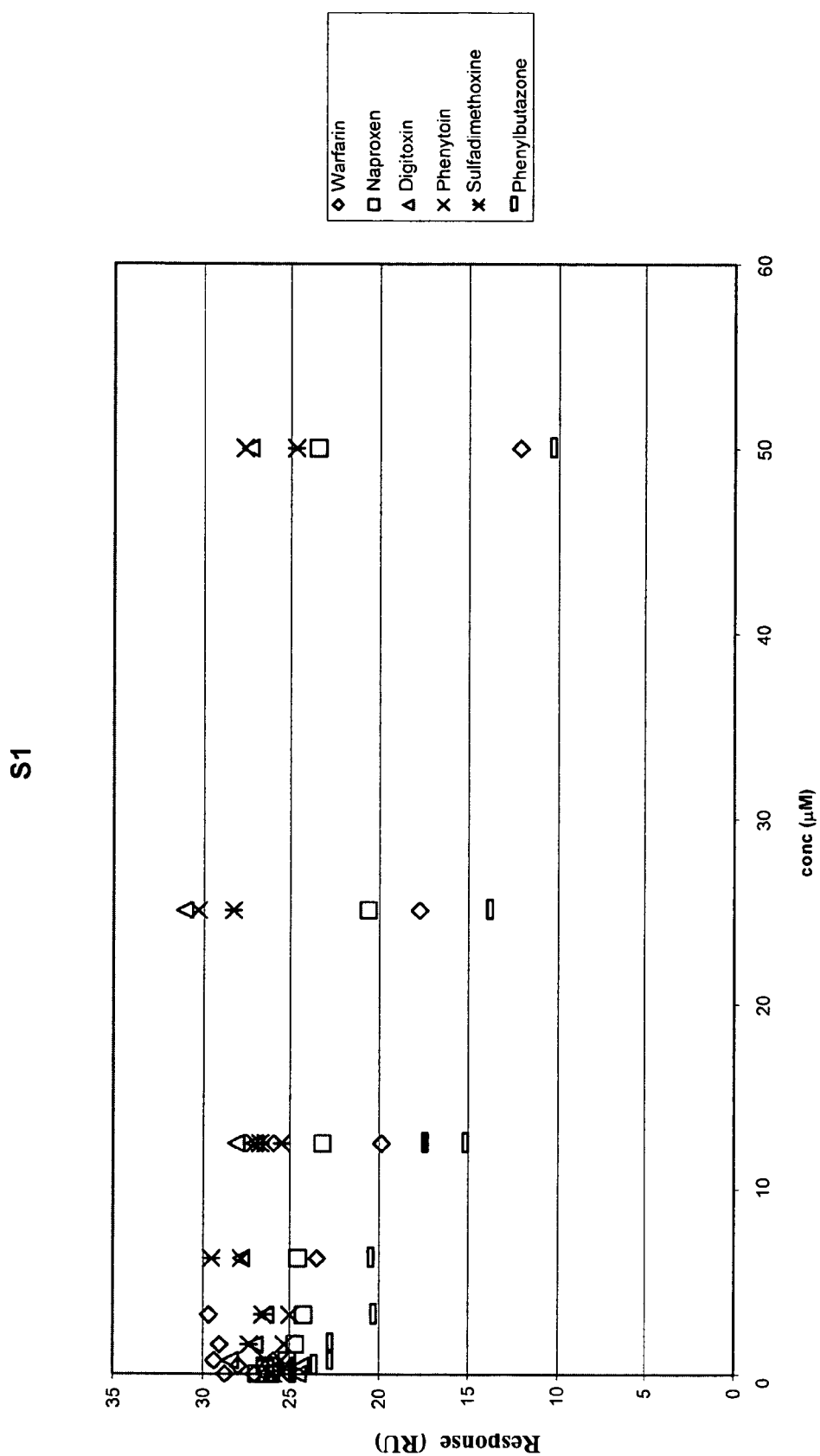
FIG. 6 is a plot of response at a defined dissociation time vs. concentration for the binding to HSA of mixtures of an analyte (S1) with three additional reference ligands (phenyloin, sulfadimethoxine and phenylbutazone, respectively).

The experiment was repeated with compound S1 and some additional compounds with known site specificities, viz. phenyloin (Mw 252; binds to site II, like naproxen), sulfadimethoxine (Mw 310; binds to site I, like warfarin) and phenylbutazone (binds to site I, like warfarin), all from Sigma (U.S.A.). The response in the stability late (d2) report point plotted versus concentration is shown in FIG. 6. Here, phenylbutazone and phenyloin, as expected, follow the behaviour of warfarin and naproxen respectively. Sulfadimethoxine, however, deviates from the behaviour of warfarin, although they are supposed to bind the same site.

Figure 7:
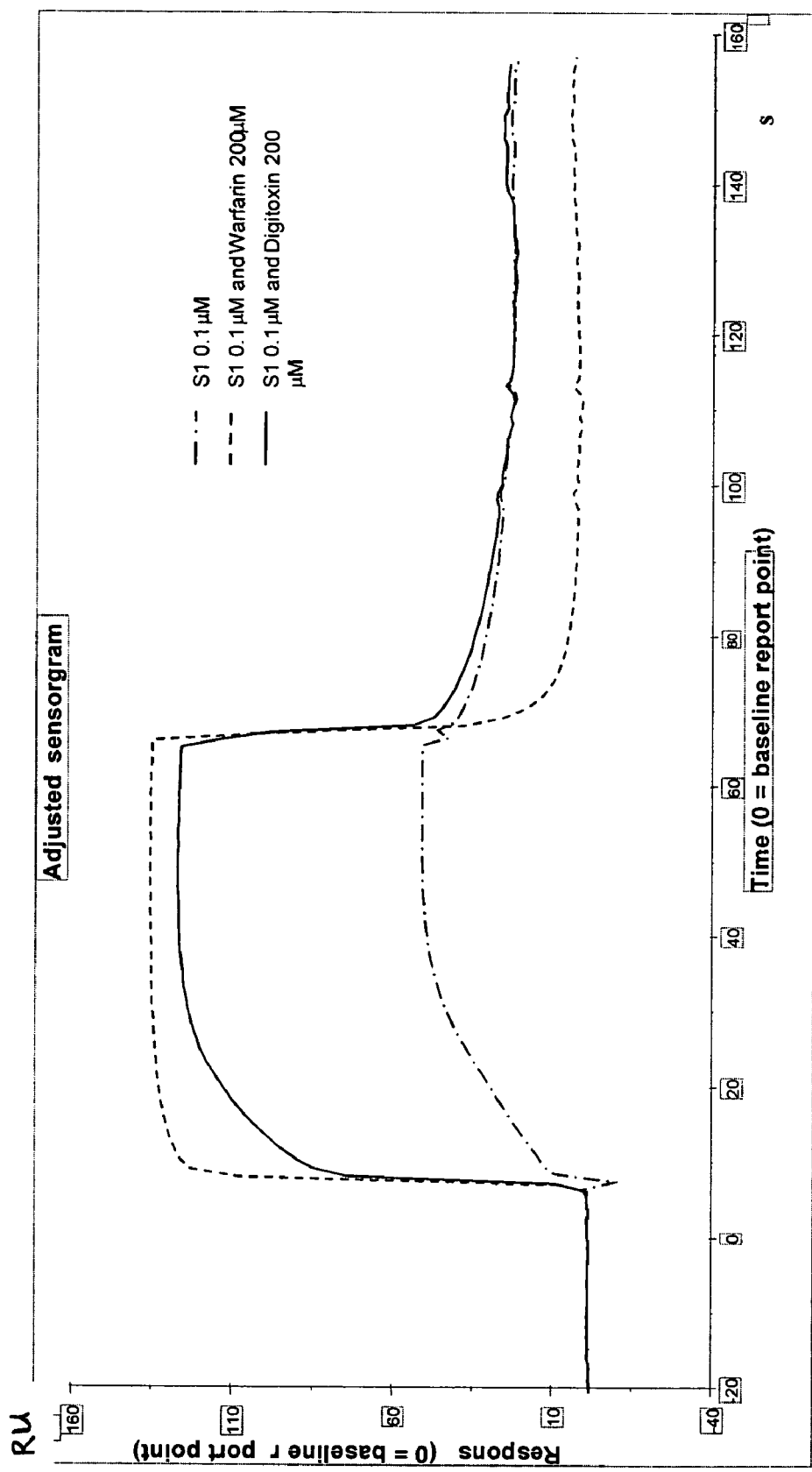
FIG. 7 is an overlay sensorgram with three superposed binding curves for the binding to HSA of an analyte (S1) and for mixtures thereof with warfarin and digitoxin, respectively.

FIG. 7 shows whole binding curves for compound S1 at 0.1 µM, alone as well as mixed with warfarin at 200 µM and digitoxin at 200 µM, respectively. As shown in the figure, compound S1 has visible association and dissociation phases. When S1 is mixed with digitoxin, the dissociation phase does not change much. Warfarin, on the other hand, extinguishes the dissociation curve of compound S1, which indicates that the two compounds are competing for the same binding site.

B. Example 2

Binding Studies of Low Molecular Weight Kinase Inhibitors

Capture of a Protein Kinase on a Sensor Chip

100 µg/ml of of Penta-His™ antibody, BSA-free (Qiagen, Venlo, Netherlands) in 0.15 M NaCl was diluted to 30 µg/ml in 10 mM sodium acetate buffer pH 5.0 and immobilized on a Series S Sensor Chip CM5 by amine coupling according to the manufacturer's instructions. The contact time was 10 min, the flow rate was 10 µl/min, and 10 mM PBS was used as running buffer. A little less than 12000 RU of antibody were immobilized.

A protein kinase ($M_w$ 33, pI 6.5) with a C-terminal His-tag (Schering A G, Berlin, Germany), 0.34 mg/ml in 50 mM MES/Hepes pH 7.3 and 200 mM NaCl, was diluted 10 times to 34 µg/ml in running buffer (10 mM PBS), and then injected over the antibody for 3 min at a flow rate of 5 µl/min, followed by 2.5 minutes injection of EDC/NHS and ethanolamine-HCl to stabilize the baseline. A little more than 4000 RU of the kinase were captured.

Profiles of Binders Against Captured Protein Kinase

Four lead inhibitor compounds, designated below as inhibitors A to D, targeted against the above captured protein kinase, and ATP (adenosine triphosphate) were injected over the captured protein kinase at a single concentration, viz. 1 µM for inhibitor A, 10 µM for inhibitor B, 1 µM for inhibitor C, 0.5 µM for inhibitor D, and 10 µM for ATP.

As running buffer was used 50 mM Tris, 150 mM NaCl, 10 mM $MgCl_2$, 1 mM $MnCl_2$ and 3% DMSO. Each cycle consisted of a 60 s sample injection, and a 60 s dissociation time, flow rate 30 µl/min. Washing was made with 50% DMSO.

Figure 8:
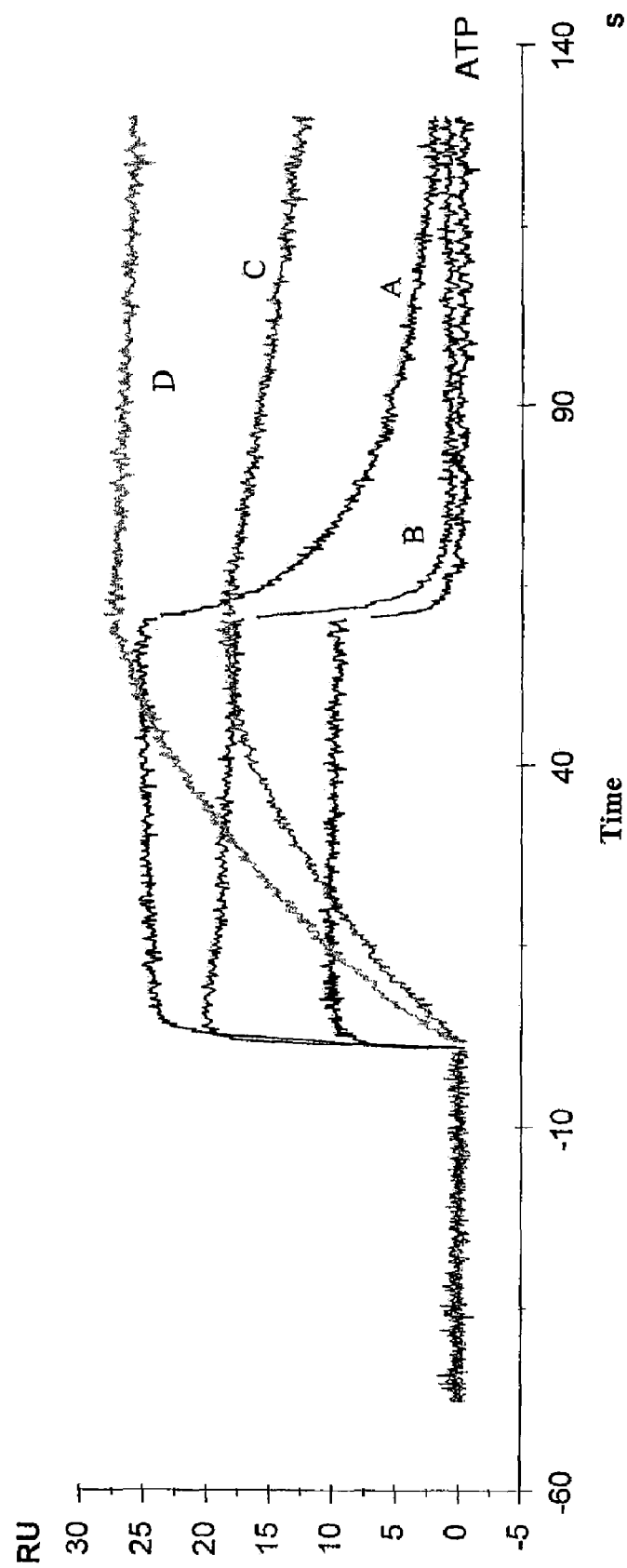
FIG. 8 is an overlay sensorgram with five superposed binding curves for the binding to a protein kinase of four inhibitors A-D and ATP.

The sensorgrams obtained are shown in overlay plot in FIG. 8, the response being plotted in resonance units (RU) against time, over the entire course of the interactions. As shown in FIG. 8, all the substances tested showed specific binding to the kinase, but with significant variations in binding profiles. Even with this single analyte concentration screen, important differences in the association and dissociation phases of the binding curves could clearly be distinguished, the four inhibitors spanning a wide range of affinities; compare, e.g., curves B and D in FIG. 8. Also of note was the very rapid binding and dissociation profile ("square wave" profile) exhibited by ATP.

Comparison of Protein Kinase Binding Specificity of ATP and Inhibitor A

Figure 9:
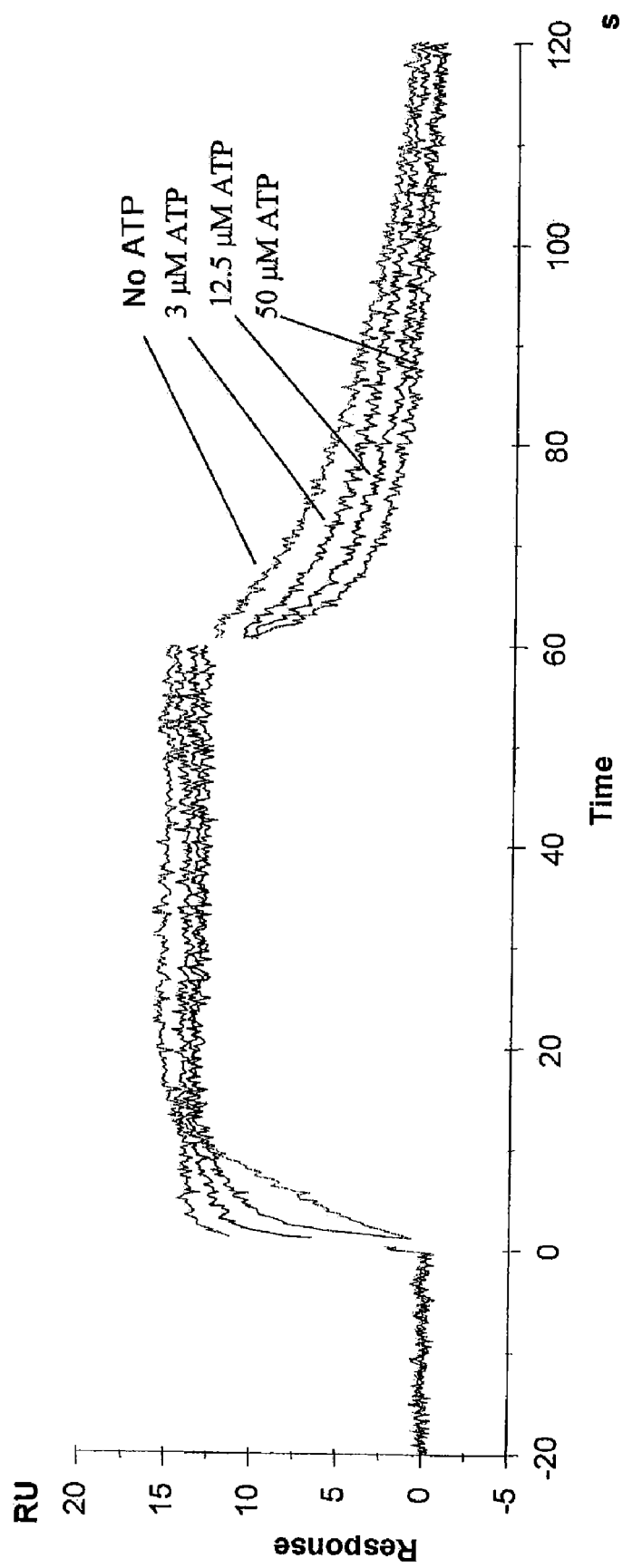
FIG. 9 is an overlay sensorgram with four superposed binding curves for the competing binding to a protein kinase of an inhibitor A and ATP at increasing concentrations of ATP.

Mixed samples containing a fixed concentration of inhibitor A (0.125 µM) and an increasing concentration of ATP (0, 3, 12.5 and 50 µM) were injected over the kinase sensor surface. The resulting sensorgrams are shown in overlay plot in FIG. 9. As appears from FIG. 9, increasing the concentration of ATP produced a significant change in the interaction profile, and particularly on the dissociation phase. It can therefore be concluded that ATP and inhibitor A compete for the binding to the kinase and that they must therefore share a common binding site (or have over-lapping binding sites), as has been observed previously for many other protein kinase inhibitors.

Comparison of Protein Kinase Binding Specificity of Inhibitor A and Inhibitor B

Figure 10:
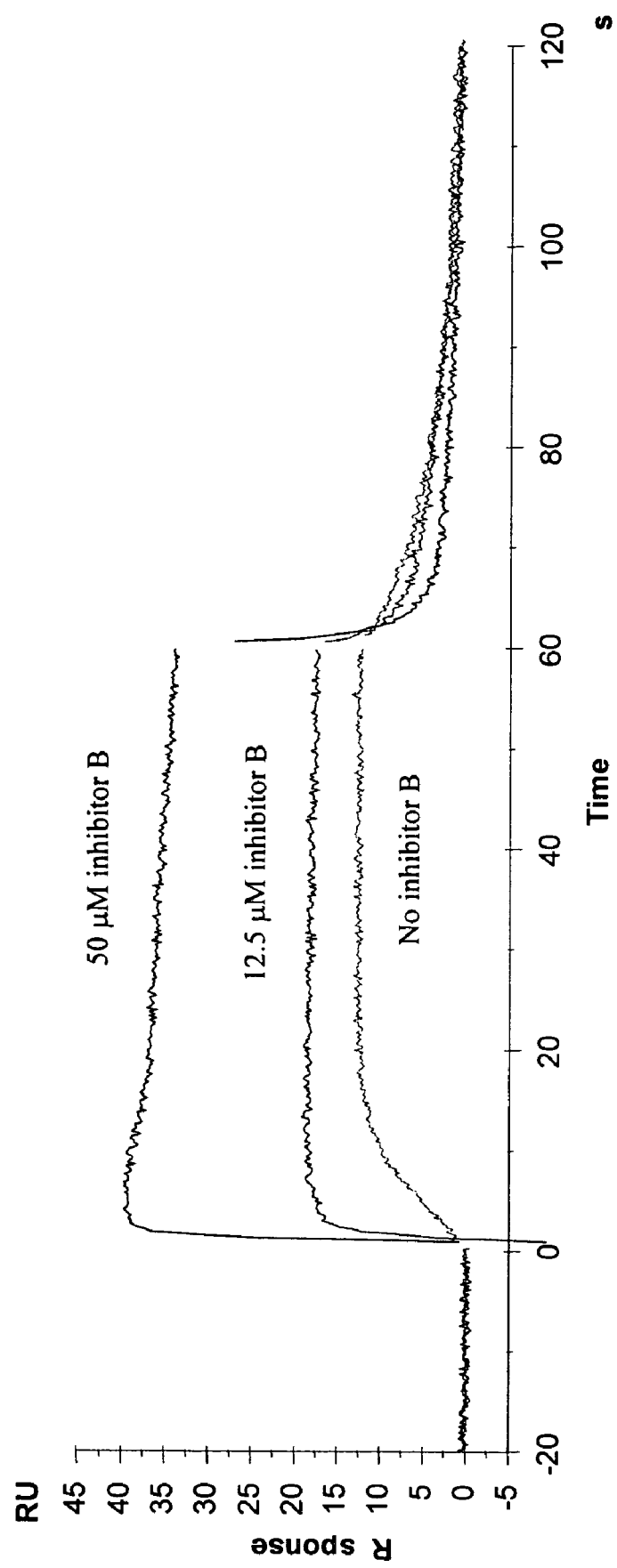
FIG. 10 is an overlay sensorgram with three superposed binding curves for the competing binding to a protein kinase of inhibitor A and inhibitor B at increasing concentrations of inhibitor B.

Mixed samples containing a fixed concentration of inhibitor A (0.125 µM) and increasing concentrations of inhibitor B (0, 12.5 and 50 μM) were injected over the kinase sensor surface. The resulting sensorgrams are shown in overlay plot in FIG. 10. As appears from FIG. 10, increasing the amount of inhibitor B. caused an increasing rapid dissociation profile that was characteristic for inhibitor B, rather than inhibitor A (cf. FIG. 8). Together, these results indicate that the two inhibitors compete with ATP for binding to a common site on the protein kinase, although with quite distinct binding kinetics.

It is to be understood that the invention is not limited to the particular embodiments of the invention described above, but the scope of the invention will be established by the appended claims.

The invention claimed is:

1. A method of determining the binding site specificity of a first analyte that binds to a ligand having at least two different binding sites, comprising:
   immobilizing the ligand to a sensing surface of a biosensor,
   providing a second, reference analyte which binds reversibly to the ligand at a binding site thereof and which is selected to have a dissociation phase, after interaction with the ligand has ceased, that is either substantially faster or substantially slower than that of the first analyte,
   contacting a mixture of the first analyte and the second, reference analyte with the immobilized ligand to permit association to the ligand,
   stopping the contacting of the first analyte and the second, reference analyte with the ligand, and subjecting the immobilized ligand to conditions which permit dissociation of bound first analyte and second reference analyte therefrom,
   monitoring in real time by a label-free detection technique at least the dissociation phase of the interaction of the mixture of the first analyte and the second, reference analyte with the immobilized ligand to obtain a dissociation phase binding curve,
   successively increasing the concentration in the mixture of the one of the first analyte and the second, reference analyte that has the faster dissociation phase, and
   determining, from a label-free detection technique, the influence of the increased concentration on the dissociation phase binding curve profile of the mixture to determine therefrom if the first analyte and the second, reference analyte bind to the same or different binding sites on the ligand,
   wherein an influence in which a substantially reduced contribution to the dissociation phase binding curve profile for the mixture from the one of the first analyte and the second, reference analyte that has the slower dissociation phase indicates that the first analyte and the second, reference analyte bind to the same binding site.

2. The method according to claim 1, wherein the second, reference analyte binds to a known binding site of the ligand.

3. The method according to claim 1, wherein the second, reference analyte has a faster dissociation phase than that of the first analyte.

4. The method according to claim 3, wherein the association and dissociation phases of the second, reference analyte are represented by a square wave type binding curve, and the association and dissociation phases of the first analyte are represented by a binding curve having visible association and dissociation phases.

5. The method according to claim 1, wherein the second, reference analyte has a slower dissociation phase than that of the first analyte.

6. The method according to claim 5, wherein the association and dissociation phases of the first analyte are represented by a square wave type binding curve, and the association and dissociation phases of the second, reference analyte are represented by a binding curve having visible association and dissociation phases.

7. The method according to claim 1, wherein the method is repeated with at least one other reference analyte that binds specifically to a different binding site on the ligand.

8. The method according claim 1, wherein the biosensor is an optical biosensor.

9. The method according to claim 8, wherein the biosensor is based on evanescent wave sensing.

10. The method according to claim 8, wherein the biosensor is based on surface plasmon resonance (SPR).

11. The method according to claim 1, wherein the first analyte and each of the second, and other reference analyte are contacted with the sensing surface in a flow cell.

12. The method according to claim 1, wherein the ligand is serum albumin.

13. The method according to claim 1, wherein the ligand is a protein kinase.

14. The method according to claim 1, wherein the ligand is a drug target.

15. The method according to claim 1, wherein the method is computer implemented.

16. The method according to claim 1, wherein the ligand is human serum albumin (HSA).

* * * * *